United States Patent
Hong

(10) Patent No.: US 8,460,613 B2
(45) Date of Patent: Jun. 11, 2013

(54) UNIFORM ELECTRICAL FIELD DIELECTRIC BARRIER DISCHARGE REACTOR

(76) Inventor: Kun-Liang Hong, Tainan (TW)

(*) Notice: Subject to any disclaimer, the term of this patent is extended or adjusted under 35 U.S.C. 154(b) by 58 days.

(21) Appl. No.: 13/171,568

(22) Filed: Jun. 29, 2011

(65) Prior Publication Data

US 2012/0000782 A1    Jan. 5, 2012

(30) Foreign Application Priority Data

Jul. 5, 2010   (CN) .......................... 2010 1 0217588

(51) Int. Cl.
    *B01J 19/08*   (2006.01)
(52) U.S. Cl.
    USPC .................................................. 422/186.04
(58) Field of Classification Search
    USPC .................................................. 422/186.04
    See application file for complete search history.

(56) References Cited

U.S. PATENT DOCUMENTS

| 6,245,299 B1 * | 6/2001 | Shiloh et al. ................... 422/121 |
| 6,852,200 B2 * | 2/2005 | LaBarge et al. ................ 204/177 |
| 7,163,663 B2 * | 1/2007 | Carlow et al. ............. 422/186.04 |

* cited by examiner

*Primary Examiner* — Kishor Mayekar
(74) *Attorney, Agent, or Firm* — Rosenberg, Klein & Lee

(57) ABSTRACT

A uniform electrical field dielectric barrier discharge reactor consists of an electrode unit, a dielectric catalyst container and an insulative housing. Each electrode plate of the electrode unit includes an insulative plane frame structure, and discharge needles evenly distributed on the insulative plane frame structure. The dielectric catalyst container is a hollow solid member internally coated with a metallic catalyst coating layer. The flow directing plate is made of a conducting substrate, having two opposite sides thereof covered by a metallic catalyst coating layer. The invention is practical for use in an air purifier, fluid sterilizer or waste water treatment equipment.

7 Claims, 9 Drawing Sheets

UNIFORM ELECTRICAL FIELD DIELECTRIC BARRIER DISCHARGE REACTOR

BACKGROUND OF THE INVENTION

1. Field of the Invention

The present invention relates to dielectric barrier discharge reactors and more particularly, to a uniform electrical field dielectric barrier discharge reactor practical for use in an air purifier, fluid sterilizer or waste water treatment equipment.

2. Description of the Related Art

Using dielectric barrier discharge to decompose benzene, xylene and other harmful organic substances in air has been well reported by many researchers. China Environmental Science, Volume VI, issued in 2001, entitled "Decomposition of benzene and xylene under normal atmospheric pressure", introduces the application of dielectric barrier discharge to decompose benzene and xylene in a flow of gas flowing under normal atmospheric pressure. There are studies using high voltage discharge to treat waste water. However these studies are still under experimentation, not for practical commercial application. For example, the issue of "The Application of Formal Safety Assessment on FPSO's Operation" in 2003, Dalian University of Technology, discloses an experimental study on the application of a dielectric barrier discharge reactor in water treatment. These studies simply introduce the application of a dielectric barrier discharge reactor in air purification or water treatment. They do not teach any measures to improve the performance of a dielectric barrier discharge reactor, for example, to generate a uniform electrical field.

Conventional dielectric barrier discharge reactors include a spiral tube type and a packed bed type. These designs have a substantially similar basic architecture. As the electrical field generated during their operation is not uniform, the treatment result is not satisfactory. A high concentration of ozone will exist during generation of an electrical field.

SUMMARY OF THE INVENTION

The present invention has been accomplished under the circumstances in view. It is the main object of the present invention to provide a uniform electrical field dielectric barrier discharge reactor, which is inexpensive to manufacture and effective in decomposition of total volatile organic compounds (TVOCs) such as formaldehyde, benzene, ammonia and etc. in the gas (air) passing therethrough flowing therethrough, and therefore it can kill any bacteria in the gas or fluid flowing therethrough and decompose any oil and smoke or harmful gaseous substances, and can be designed for use in an air purifier, fluid sterilizer or waste water treatment equipment.

To achieve this and other objects of the present invention, a uniform electrical field dielectric barrier discharge reactor includes an electrode unit consisting of a positive electrode plate and a negative electrode plate, a dielectric catalyst container set between the positive and negative electrode plates, a flow directing plate mounted in the dielectric catalyst container, and an insulative housing accommodating the positive and negative electrode plates and the dielectric catalyst container and defining an input port and an output port. The electrode unit includes an insulative plane frame structure, and discharge needles evenly distributed on the insulative plane frame structure. The positive and negative electrode plates have different polarity and are arranged in a parallel manner at two opposite sides relative to the dielectric catalyst container. The dielectric catalyst container is a hollow solid member internally coated with a metallic catalyst coating layer. The flow directing plate is made of a conducting substrate, having two opposite sides thereof covered by a metallic catalyst coating layer.

DETAILED DESCRIPTION OF THE PREFERRED EMBODIMENT

Figure 1:
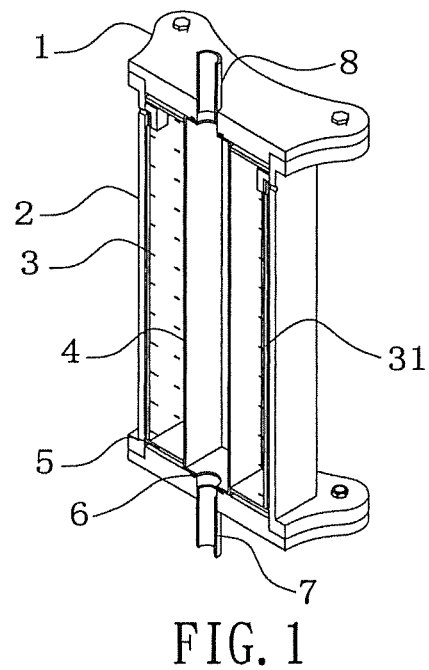
FIG. 1 is a sectional elevational view of a dielectric barrier discharge reactor in accordance with the present invention.

Referring to FIGS. 1-5, a uniform electrical field dielectric barrier discharge reactor in accordance with the present invention basically comprises at least one electrode unit each consisting of a positive electrode plate 3 and a negative electrode plate 31, a dielectric catalyst container 4 set between the positive electrode plate 3 and the negative electrode plate 31 and accommodating therein a flow directing plate 41 carrying a catalyst coating layer 42, an insulative housing 2 housing the positive electrode plate 3, the negative electrode plate 31 and the dielectric catalyst container 4 and defining an input port 7 and an output port 8, and an insulative connector 1, sealing blocks 5 and seal rings 6.

The electrode unit is based on an insulative frame structure, as shown in FIG. 7, FIG. 8, FIG. 9 and FIG. 10. The positive electrode plate 43 and the negative electrode plate 44 each comprise an electrode plate material 441, an insulative material 442, a plurality of discharge needles 45, a grounding contact 9 at the bottom side, and a circuit 46 embedded therein. The positive electrode plate 43 and the negative electrode plate 44 are selectively configured within the range of 100 mm~5000 mm×100 mm~5000 mm.

The positive electrode plate 43 and the negative electrode plate 44 each have a plurality of discharge needles 45 evenly arranged thereon and electrically connected to the circuit 46 that is embedded in the electrode plate 43;44. The positive electrode plate 3 and the negative electrode plate 31 have different polarity and are respectively arranged at two opposite sides of the dielectric catalyst container 4 (see FIG. 2) in a parallel manner. The distance between the needle points of the discharge needles 45 and the dielectric catalyst container 4 (see FIG. 2) is maintained within 5 mm~60 mm. The discharge needles 45 of the positive electrode plate 3 respectively correspond to that of the negative electrode plate 31. The size and volume of the dielectric catalyst container 4 (see FIG. 2) are directly proportional to the power of the power supply provided.

Figure 2:
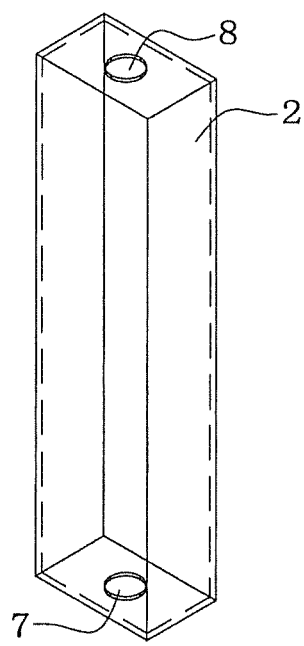
FIG. 2 is a perspective view of the dielectric catalyst container of the dielectric barrier discharge reactor in accordance with the present invention.
Figure 3:
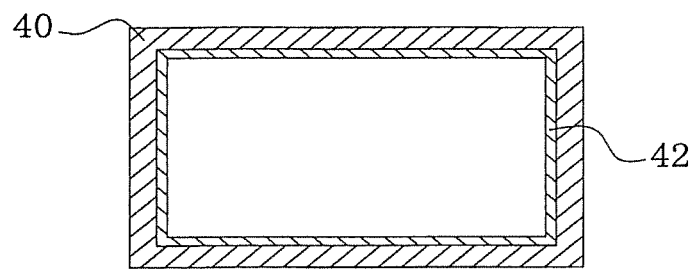
FIG. 3 is a cross sectional view of the dielectric catalyst container of the dielectric barrier discharge reactor in accordance with the present invention.
Figure 4:
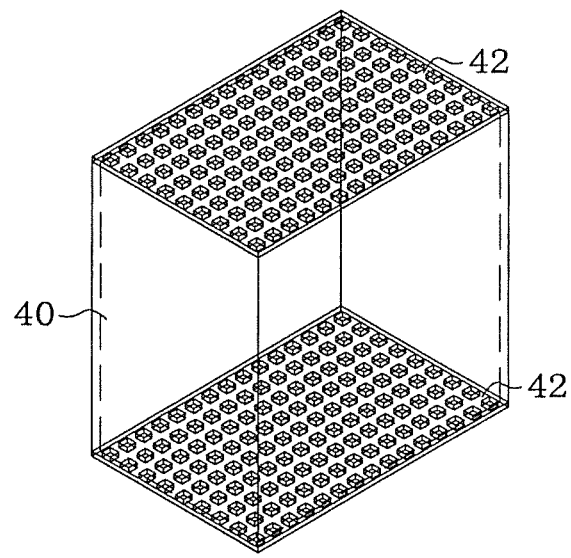
FIG. 4 is a perspective view illustrating the frame structure of the dielectric catalyst container in accordance with the present invention.
Figure 5:
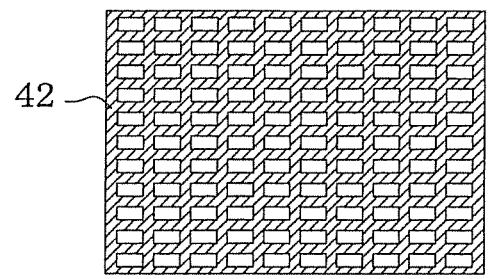
FIG. 5 is a cross sectional view of the top of the frame structure of the dielectric catalyst container in accordance with the present invention.

The dielectric catalyst container 4 (see FIG. 2) is a solid storage device in rectangular, spherical or any other irregular shape. The plain view size of the dielectric catalyst container 4 is equal to the electrode unit. The catalyst coating layer 42 of the dielectric catalyst container 4 is selected from the group of gold, silver, platinum, nickel, magnesium, chrome and their oxides. FIG. 2 and FIG. 4 illustrate two alternate forms of the dielectric catalyst container 4. The frame structure 40 of the dielectric catalyst container 4 is a conducting substrate. The catalyst coating layer 42 is coated on the inner side of the dielectric catalyst container 4.

Figure 11:
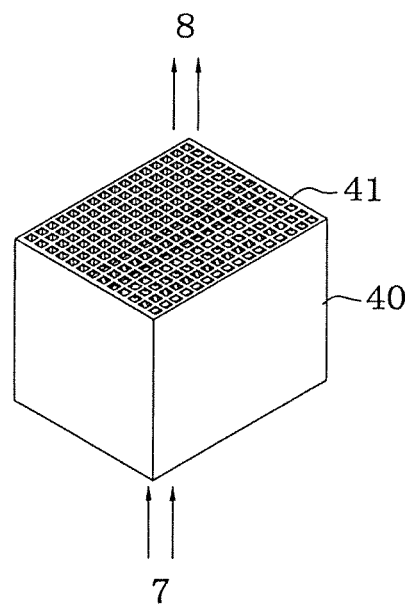
FIG. 11 is an elevational view illustrating one example of the arrangement of a flow directing plate in the dielectric catalyst container in accordance with the present invention.
Figure 12:
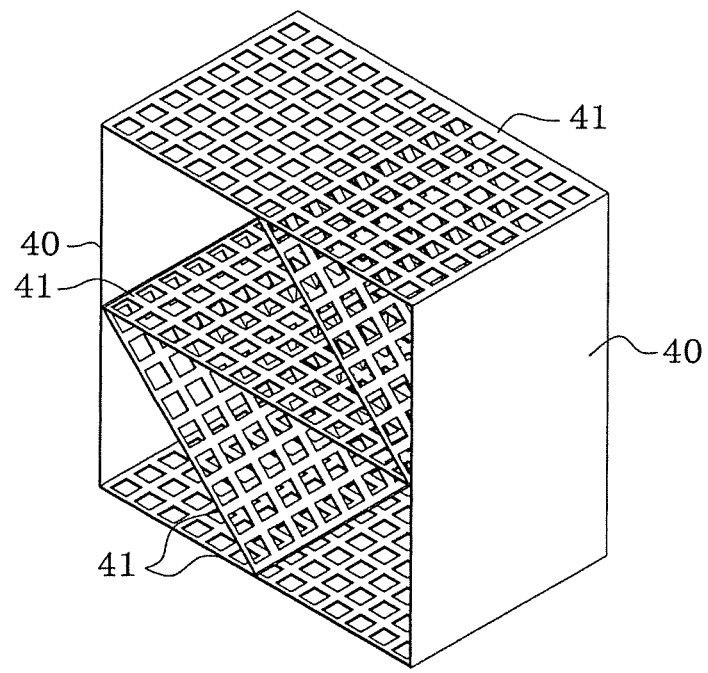
FIG. 12 is an elevational view illustrating another example of the arrangement of a flow directing plate in the dielectric catalyst container in accordance with the present invention.
Figure 13:
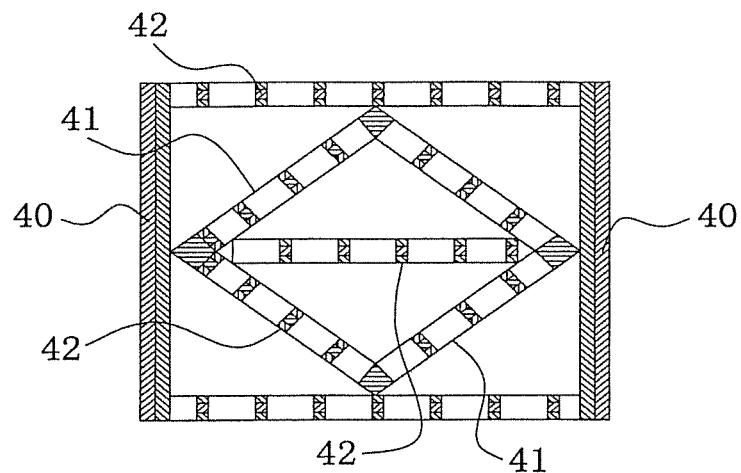
FIG. 13 is a sectional view of the flow directing plate shown in FIG. 11.
Figure 15:
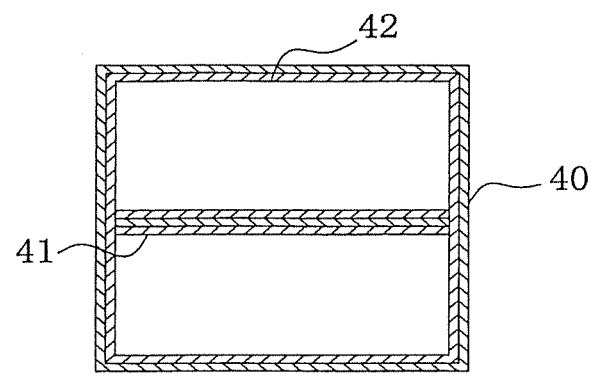
FIG. 15 is a sectional view of the flow directing plate shown in FIG. 14.
Figure 17:
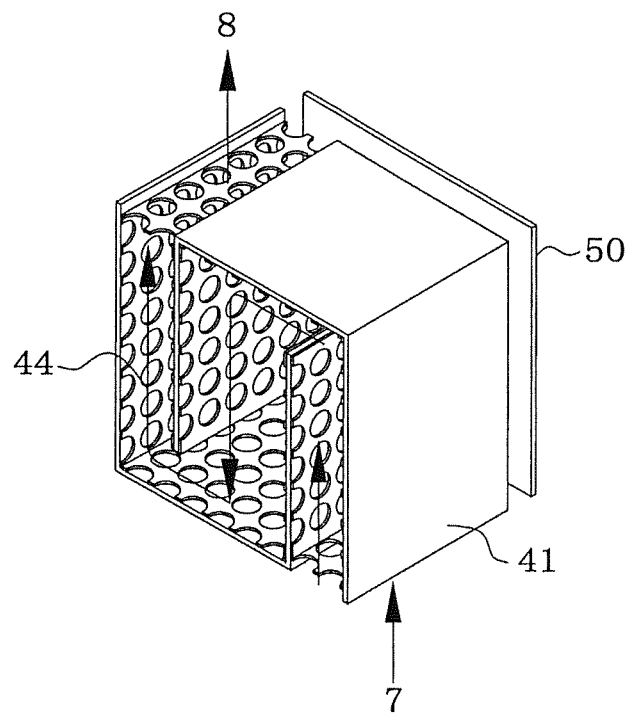
FIG. 17 is a schematic drawing illustrating the flow path defined in the flow directing plate shown in FIG. 16.

To increase the chance of contact between the applied fluid and the dielectric, the flow directing plate 41 is arranged on the inside of the dielectric catalyst container 4 (see FIG. 2), enhancing the performance of the dielectric barrier discharge reactor. The flow directing plate 41 and the dielectric catalyst container 4 are selected from the same material with the exception that the flow directing plate 41 has its both sides covered by the catalyst coating layer 42. FIG. 12, FIG. 13 and FIG. 15 illustrate various alternate forms of the flow directing plate 41. FIG. 12 illustrates the internal structure of FIG. 11, in which the flow directing plate 41 exhibits a rhombic structure; the gas (or fluid) under treatment flows through the rhombic structure of the flow directing plate 41. FIG. 13 illustrates the flow directing plate 41 exhibits a wavelike configuration and extends along the axis between the input port 7 and the output port 8. The flow directing plate 41 is made of a conducting substrate, having its both sides covered by the catalyst coating layer 42. The flow directing plate 41 can be made in a rhombic or wavelike configuration and arranged inside the frame structure 40. FIG. 15 illustrates the flow directing plate 41 arranged in a deflected style, defining a deflection passage for the passing of the applied gas (or fluid) to extend the gas (fluid) retention time. The flow path 50 defined in the flow directing plate 41 is illustrated in FIG. 17.

When applying a high voltage direct current to the at least one electrode unit, two electrode units are respectively connected to the positive terminal and negative terminal, or respectively connected to the negative terminal and the ground terminal, causing point-to-point electrical discharge between the respective discharge needles 45 at the positive electrode plate 3 and the respective discharge needles 45 at the negative electrode plate 31. Under a high voltage between respective discharge needles, dielectric barrier discharge is performed, causing positive ions and negative ions to be neutralized rapidly in the dielectric hollow barrier body. At this time, ions are transferred through the dielectric of the hollow barrier body. The hollow dielectric is a good conductor for even discharge of electricity to produce strong energy. The strong discharge energy is effective in decomposition of the organic gas or organic solvent flowing through the dielectric hollow barrier body, and therefore it can kill any bacteria in the gas or fluid flowing therethrough and decompose any oil and smoke or harmful gaseous substances.

During a gas treatment application of the present invention, benzene, formaldehyde and other harmful gaseous substances passing through the dielectric barrier discharge reactor will be ionized and rapidly oxidized into negative ions and then reduced to oxygen, water and carbon dioxide when combined with air. At the same time, an electrical field is produced between the two electrode units. The dielectric hollow barrier body between the two electrode units is induced by the electrical field, causing the catalyst coating layer 42 to generate metallic ions. When the applied gas (air) flows through the reactor, the catalyst coating layer 42 is induced by the electrical field to generate metallic ions that effectively reduce the content of total volatile organic compounds (TVOCs) such as formaldehyde, benzene, ammonia and etc. in the gas (air) passing therethrough. Metallic ions provide a strong oxidizing and sterilizing power to continuously improve indoor air quality. The metallic ions generated by the catalyst coating layer 42 in the reactor can suppress the generation of ozone during point-to-point electrical discharge.

During a fluid sterilization application of the present invention, a strong electrical field will be produced in the dielectric hollow barrier body of the dielectric barrier reactor between the positive electrode plate 3 and the negative electrode plate 31 upon conduction of electricity to the dielectric barrier reactor. When a fluid, for example, city water or drinking water flows through the reactor, *Escherichia coli* and other bacteria in the water will be soon killed.

During a waste water treatment application of the present invention, a strong electrical field will be produced in the dielectric hollow barrier body of the dielectric barrier reactor between the positive electrode plate 3 and the negative electrode plate 31 upon conduction of electricity to the dielectric barrier reactor. The dielectric hollow barrier body between the two electrode units is induced by the electrical field, causing the catalyst coating layer 42 to generate metallic ions.

When waste water flows through the reactor, the catalyst coating layer 42 keeps generating metallic ions to effectively degrade COD (chemical oxygen demand), organic phosphorus and other toxic substances in the waste water passing therethrough, thereby purifying the waste water.

Figure 18:
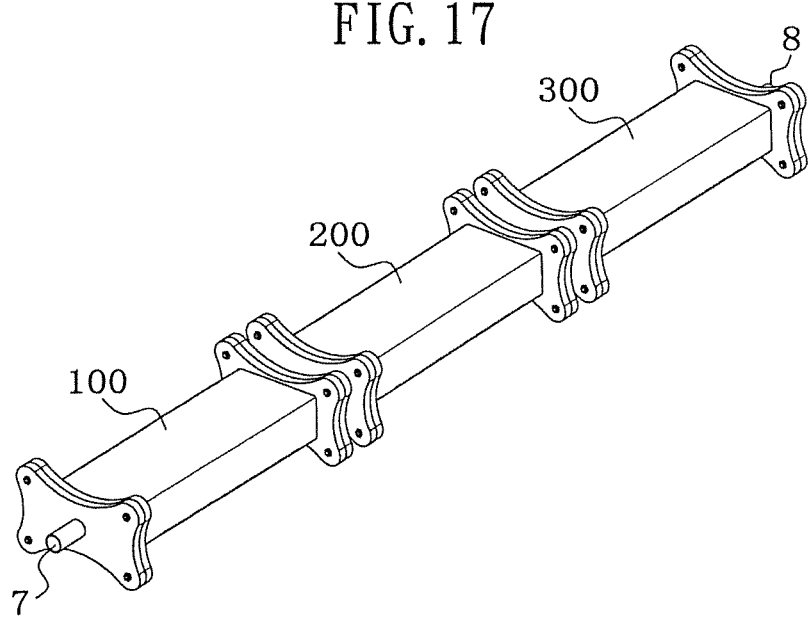
FIG. 18 is a schematic drawing illustrating a modularized high-voltage dielectric treatment unit constructed in accordance with the present invention.

A plurality of uniform electrical field dielectric barrier discharge reactors can be connected in series to form a modularized high-voltage dielectric treatment unit for multi-stage processing to fit different gas/water treatment requirements. When multiple uniform electrical field dielectric barrier discharge reactors are connected in series, the gas (fluid) input port of the first stage works as the total gas (fluid) input port, the gas (fluid) output port of the first stage is connected to the gas (fluid) input port of the second stage, the gas (fluid) output port of the second stage is connected to the gas (fluid) input port of the third stage, and so on, and the gas (air) output port of the last stage works as the total gas (fluid) output port. FIG. 18 illustrates a 3-stage modularized high-voltage dielectric treatment unit consisting of three uniform electrical field dielectric barrier discharge reactors 100;200;300 and providing enhanced treatment performance.

When compared with prior art techniques, the invention has the advantages of effective sterilization, effective TVOCs decomposition and removal and effective suppression of ozone. More particularly, uniform discharge reaction in the high-voltage discharge reactor avoids dead corner. The invention is practical for organic gas and solvent decomposition application, for the application of killing bacteria in gas or water, for the application of decomposing oil and smoke passing therethrough, as well as for the application of modifying the surface structure of polymeric materials. In general, the invention can be designed for use in an air purifier, organic waste water treatment equipment, agricultural sterilizer, medical sterilizer, kitchen sterilizer, oil/smoke decomposer and etc.

Example I

A uniform electrical field dielectric discharge reactor comprises an electrode unit consisting of a positive electrode plate 3 and a negative electrode plate 31, a dielectric catalyst container 4 set between the positive electrode plate 3 and the negative electrode plate 31, and an insulative housing 2 housing the positive electrode plate 3, the negative electrode plate 31 and the dielectric catalyst container 4 and defining an input port 7 and an output port 8. The dielectric catalyst container 4 (see FIG. 2 and FIG. 3) is a 300 mm×300 mm×1000 mm rectangular stainless steel container internally coated with a platinum/nickel catalyst coating layer 42. The dielectric catalyst container 4 further has an outlet pipe located on the top side thereof and an inlet pipe located on the bottom side thereof. The positive electrode plate 3 and the negative electrode plate 31 are respectively arranged at two opposite sides of the dielectric catalyst container 4 in a parallel manner. The positive electrode plate 3 and the negative electrode plate 31 have a plane view size of 300 mm×1000 mm. The positive electrode plate 3 and the negative electrode plate 31 each have a plurality of discharge needles 45 evenly arranged thereon. The distance between the discharge needles 45 and the dielectric catalyst container 4 (see FIG. 2) is 50 mm. The applied voltage is 50 KV. This embodiment is practical for waste water treatment.

Example II

A uniform electrical field dielectric discharge reactor comprises an electrode unit consisting of a positive electrode plate 3 and a negative electrode plate 31, a dielectric catalyst container 4 (see FIG. 8), and an insulative housing 2 housing the positive electrode plate 3, the negative electrode plate 31 and the dielectric catalyst container 4 and defining an input port 7 and an output port 8. The dielectric catalyst container 4 (see FIG. 8) is a cylindrical stainless steel container internally. The dimension of the internal chamber of the dielectric catalyst container 4 is Φ200 mm×1000 mm. The dielectric catalyst container 4 is fixedly connected between a top mounting plate 47 and a bottom mounting plate 48. The dielectric catalyst container 4 has its inside wall coated with a platinum/nickel catalyst coating layer 42. The dielectric catalyst container 4 further has an outlet pipe located on the top side thereof and an inlet pipe located on the bottom side thereof. The positive electrode plate 3 and the negative electrode plate 31 are respectively arranged at two opposite sides of the dielectric catalyst container 4 in a parallel manner (see FIG. 8). The positive electrode plate 3 and the negative electrode plate 31 are transversely arched members of size Φ250 mm×1000 mm (height)×180 mm (width). The positive electrode plate 3 and the negative electrode plate 31 each have a plurality of discharge needles 45 evenly and perpendicularly arranged on the inner surface thereof. The distance between the discharge needles 45 and the dielectric catalyst container 4 is 30 mm. The applied voltage is 20 KV. This embodiment is practical for sterilizing city water, milk and drinking water.

Example III

Figure 6:
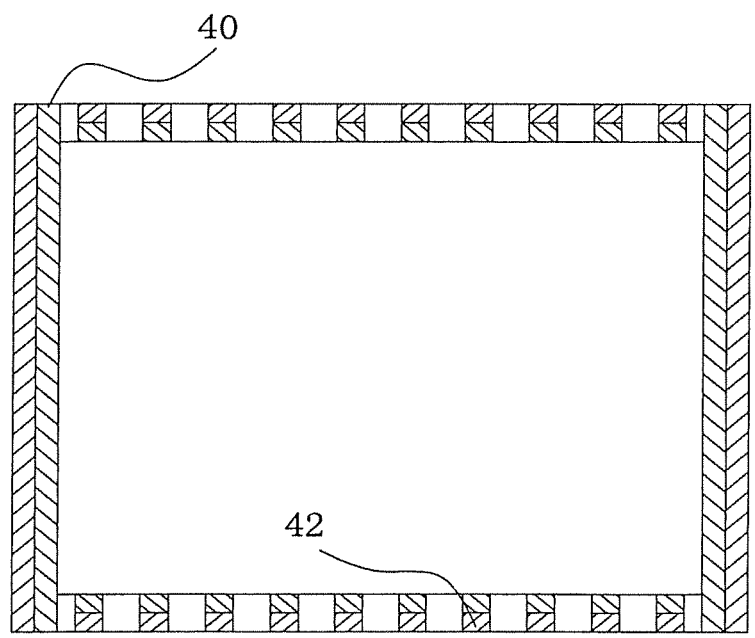
FIG. 6 is a longitudinal sectional view of the frame structure of the dielectric catalyst container in accordance with the present invention.
Figure 7:
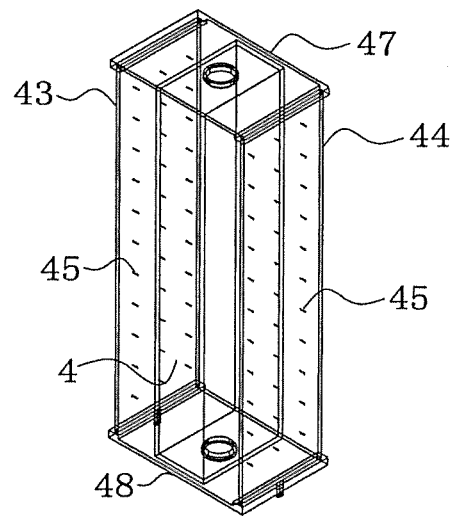
FIG. 7 illustrates a rectangular dielectric catalyst container for dielectric barrier discharge reactor in accordance with the present invention.
Figure 8:
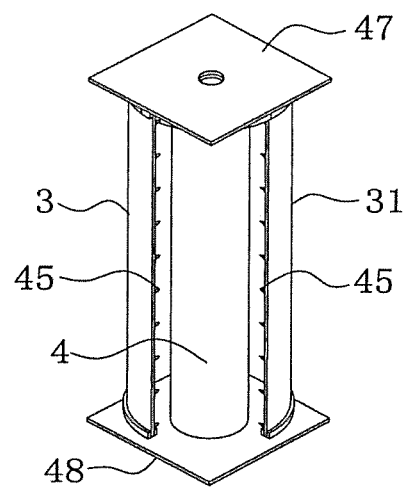
FIG. 8 illustrates a cylindrical dielectric catalyst container for dielectric barrier discharge reactor in accordance with the present invention.
Figure 9:
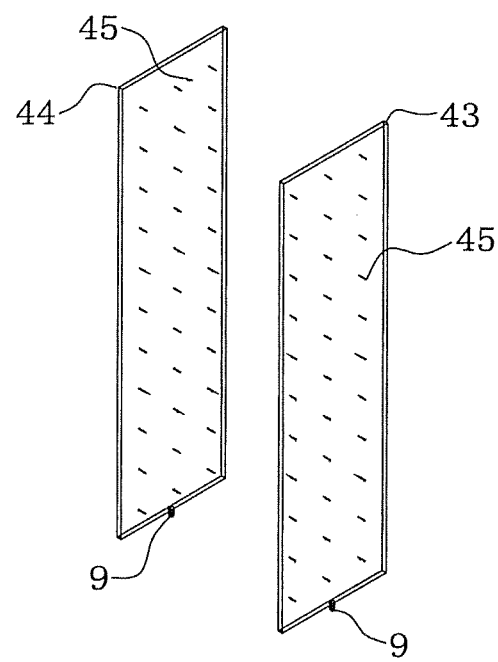
FIG. 9 is a schematic drawing illustrating the structural arrangement of the positive and negative electrode plates in accordance with the present invention.
Figure 10:
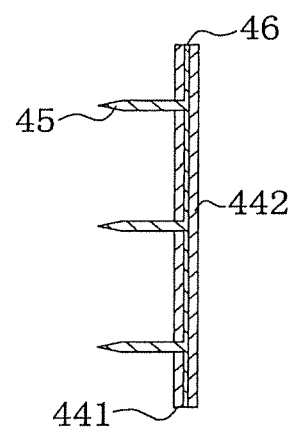
FIG. 10 is a sectional view of the positive (negative) electrode plates in accordance with the present invention.
Figure 16:
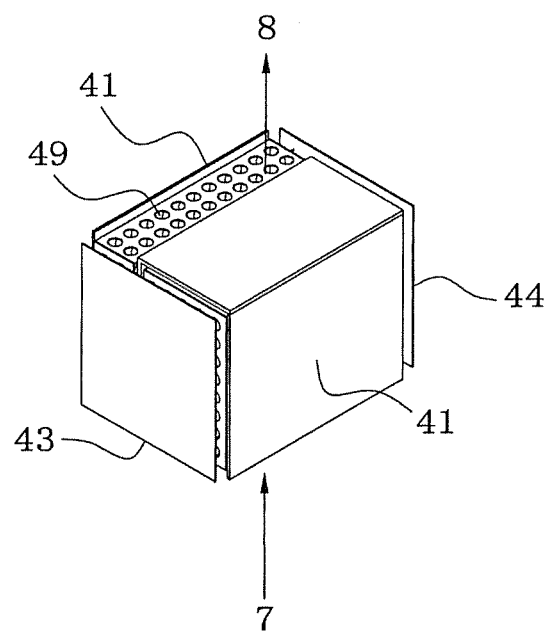
FIG. 16 is an elevational view illustrating still another example of the arrangement of a flow directing plate in the dielectric catalyst container in accordance with the present invention.

A uniform electrical field dielectric discharge reactor comprises an electrode unit consisting of a positive electrode plate 3 and a negative electrode plate 31, a dielectric catalyst container 4 (see FIG. 4) set between the positive electrode plate 3 and the negative electrode plate 31 and accommodating therein a flow directing plate 41, and an insulative housing 2 housing the positive electrode plate 3, the negative electrode plate 31 and the dielectric catalyst container 4 and defining an input port 7 and an output port 8. The dielectric catalyst container 4 (see FIG. 4, FIG. 5 and FIG. 6) is a 200 mm×300 mm×800 mm rectangular, grilled aluminum container internally coated with a platinum/nickel catalyst coating layer 42. The dielectric catalyst container 4 further has an outlet pipe located on the top side thereof and an inlet pipe located on the bottom side thereof. The flow directing plate 41, as shown in FIG. 16 and FIG. 17, is a deflected flow directing plate mounted inside the dielectric catalyst container 4 and having a dimension slightly smaller than the internal chamber of the dielectric catalyst container 4. The positive electrode plate 3 and the negative electrode plate 31 are respectively arranged at two opposite sides of the dielectric catalyst container 4 in a parallel manner. The positive electrode plate 3 and the negative electrode plate 31 have a plane view size of 300 mm×800 mm. The positive electrode plate 3 and the negative electrode plate 31 each have a plurality of discharge needles 45 evenly arranged thereon. The distance between the discharge needles 45 and the dielectric catalyst container 4 (see FIG. 2) is 35 mm. The applied voltage is 30 KV. This embodiment is practical for air purification application.

Example IV

A uniform electrical field dielectric discharge reactor comprises an electrode unit consisting of a positive electrode plate 3 and a negative electrode plate 31, a dielectric catalyst container 4 (see FIG. 2) set between the positive electrode plate 3 and the negative electrode plate 31 and accommodating therein a flow directing plate 41, and an insulative housing 2 housing the positive electrode plate 3, the negative electrode plate 31 and the dielectric catalyst container 4 and defining an input port 7 and an output port 8. The dielectric catalyst container 4 (see FIG. 2 and FIG. 3) is a 500 mm×500 mm×200 mm rectangular stainless steel container internally coated with a platinum/nickel catalyst coating layer 42. The dielectric catalyst container 4 further has an outlet pipe located on the top side thereof and an inlet pipe located on the bottom side thereof. The flow directing plate 41, as shown in FIG. 11, FIG. 12 and FIG. 13, exhibits a rhombic structure, having a dimension of 400 mm×400 mm×2000 mm. The positive electrode plate 3 and the negative electrode plate 31 are respectively arranged at two opposite sides of the dielectric catalyst container 4 in a parallel manner. The positive electrode plate 3 and the negative electrode plate 31 have a plane view size of 300 mm×2000 mm. The positive electrode plate 3 and the negative electrode plate 31 each have a plurality of discharge needles 45 evenly arranged thereon. The distance between the discharge needles 45 and the dielectric catalyst container 4 (see FIG. 2) is 50 mm. The applied voltage is 50 KV. This embodiment is practical for waste water treatment.

Example V

Figure 14:
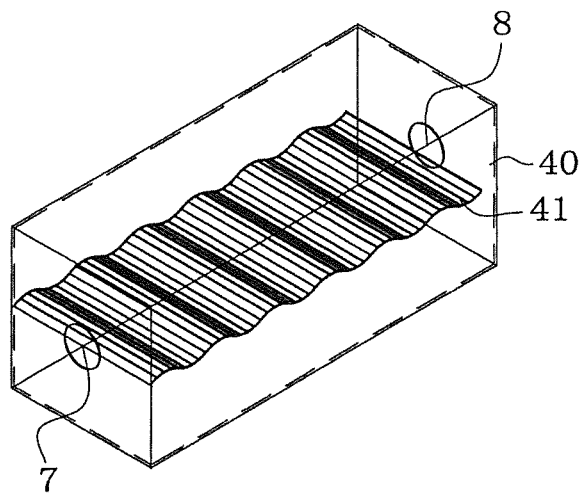
FIG. 14 is an elevational view illustrating still another example of the arrangement of a flow directing plate in the dielectric catalyst container in accordance with the present invention.

A modularized high-voltage dielectric treatment unit formed of three uniform electrical field dielectric discharge reactors connected in series. Each uniform electrical field dielectric discharge reactor comprises an electrode unit consisting of a positive electrode plate 3 and a negative electrode plate 31, a dielectric catalyst container 4 (see FIG. 2) set between the positive electrode plate 3 and the negative electrode plate 31 and accommodating therein a flow directing plate 41, and an insulative housing 2 housing the positive electrode plate 3, the negative electrode plate 31 and the dielectric catalyst container 4 and defining an input port 7 and an output port 8. The dielectric catalyst container 4 (see FIG. 2 and FIG. 3) is a 300 mm×300 mm×1000 mm rectangular stainless steel container internally coated with a platinum/nickel catalyst coating layer 42. The dielectric catalyst container 4 further has an outlet pipe located on the top side thereof and an inlet pipe located on the bottom side thereof. The flow directing plate 41, as shown in FIG. 14 and FIG. 15, exhibits a wavelike structure, having a dimension of 250 mm×250 mm×1000 mm. The positive electrode plate 3 and the negative electrode plate 31 are respectively arranged at two opposite sides of the dielectric catalyst container 4 in a parallel manner. The positive electrode plate 3 and the negative electrode plate 31 have a plane view size of 250 mm×1000 mm. The positive electrode plate 3 and the negative electrode plate 31 each have a plurality of discharge needles 45 evenly arranged thereon. The distance between the discharge needles 45 and the dielectric catalyst container 4 is 50 mm. The applied voltage is 50 KV. This embodiment is practical for waste water treatment.

Although particular embodiments of the invention have been described in detail for purposes of illustration, various modifications and enhancements may be made without departing from the spirit and scope of the invention. Accordingly, the invention is not to be limited except as by the appended claims.

What the invention claimed is:

1. A uniform electrical field dielectric barrier discharge reactor, comprising:
   an electrode unit consisting of a positive electrode plate and a negative electrode plate, said positive electrode plate and said negative electrode plate being spaced one from the other;
   a dielectric catalyst container set between said positive electrode plate and said negative electrode plate, said dielectric catalyst container being spaced from both said positive electrode plate and said negative electrode plate, said dielectric catalyst container having an inlet port and an outlet port for fluid flow therethrough;
   a flow directing plate mounted in said dielectric catalyst containers; and
   an insulative housing accommodating said positive electrode plate, said negative electrode plate and said dielectric catalyst container, said housing having an input port disposed in correspondence with said inlet port of said dielectric catalyst container and an output port disposed in correspondence with said outlet port of said dielectric catalyst container.

2. The uniform electrical field dielectric barrier discharge reactor as claimed in claim 1, wherein said electrode unit comprises an insulative plane frame structure, a plurality of discharge needles evenly distributed on said insulative plane frame structure and electrically connected in parallel to a circuit in said electrode unit; said positive electrode plate and said negative electrode plate being respectively connected to different polarities of a power supply and are arranged in a parallel manner at two opposite sides relative to said dielectric catalyst container, said positive electrode plate and said negative electrode plate each being spaced from said dielectric catalyst container by a distance within 5 mm~60 mm.

3. The uniform electrical field dielectric barrier discharge reactor as claimed in claim 2, wherein said insulative plane frame structure of said electrode unit has the size of 100 mm~5000 mm×100 mm~5000 mm.

4. The uniform electrical field dielectric barrier discharge reactor as claimed in claim 1, wherein said dielectric catalyst container is formed of solid walls and having one of a rectangular shape, a cylindrical shape or an irregular shape, said dielectric catalyst container having a plane view size equal to a size of said electrode unit and a metallic catalyst coating layer selected from a metal or metal oxide and coated on the inner surface thereof.

5. The uniform electrical field dielectric barrier discharge reactor as claimed in claim 4, wherein said metallic catalyst coating layer is selected from the material group of gold, silver, platinum, nickel, magnesium, chrome and their oxides.

6. The uniform electrical field dielectric barrier discharge reactor as claimed in claim 1, wherein said flow directing plate is made of a material in common with said dielectric catalyst container and formed in a rhombic, wavelike or deflected configuration, said flow directing plate having two opposite sides thereof covered by a metallic catalyst coating layer.

7. The uniform electrical field dielectric barrier discharge reactor as claimed in claim 1, wherein multiple uniform electrical field dielectric barrier discharge reactors are connectable in series to form a modularized high-voltage dielectric treatment unit in such a manner that the output port of the housing of one preceding uniform electrical field dielectric barrier discharge reactor is connected to the input port of the housing of the adjacent posterior uniform electrical field dielectric barrier discharge reactor.

\* \* \* \* \*